United States Patent
Krohn

(10) Patent No.: US 6,332,462 B1
(45) Date of Patent: Dec. 25, 2001

(54) METHOD AND DEVICE FOR PRODUCING RESPIRATORY AIR WHICH IS HARMLESS TO HEALTH IN POSITIVE PRESSURE NASAL BREATHING APPARATUS

(76) Inventor: Holger Krohn, Drechselblick 9, 97816 Lohr (DE)

(*) Notice: Subject to any disclaimer, the term of this patent is extended or adjusted under 35 U.S.C. 154(b) by 0 days.

(21) Appl. No.: 08/945,690
(22) PCT Filed: May 3, 1996
(86) PCT No.: PCT/EP96/01842
 § 371 Date: Nov. 3, 1997
 § 102(e) Date: Nov. 3, 1997
(87) PCT Pub. No.: WO96/34644
 PCT Pub. Date: Nov. 7, 1996

(30) Foreign Application Priority Data
 May 3, 1995 (DE) .............................. 195 15 739

(51) Int. Cl.[7] ................................................ A61M 16/00
(52) U.S. Cl. ................................ 128/204.15; 128/204.18
(58) Field of Search .................... 128/204.18, 204.15, 128/204.16

(56) References Cited

U.S. PATENT DOCUMENTS

| | | | |
|---|---|---|---|
| 3,126,003 | * 3/1964 | Steel | 128/204.16 |
| 3,999,541 | * 12/1976 | Tabor | 128/204.15 |
| 4,237,877 | * 12/1980 | Boehler | 128/204.18 |
| 5,065,756 | * 11/1991 | Rapoport | 128/204.18 |
| 5,242,403 | * 9/1993 | Falb et al. | 128/204.15 |
| 5,263,476 | * 11/1993 | Henson | 128/204.18 |
| 5,269,293 | * 12/1993 | Loser et al. | 128/204.18 |
| 5,540,219 | * 7/1996 | Mechlenburg et al. | 128/204.18 |
| 5,697,361 | * 12/1997 | Smith | 128/204.18 |

FOREIGN PATENT DOCUMENTS

WO 93/20874 * 10/1993 (WO).

* cited by examiner

*Primary Examiner*—Aaron J. Lewis
(74) *Attorney, Agent, or Firm*—Connolly Bove Lodge & Hutz LLP

(57) ABSTRACT

The invention concerns a positive pressure nasal breathing apparatus in which a processed air flow is supplied at positive pressure to the person to be treated. The apparatus comprises: a first device (10) for producing a first air flow which has a given first temperature and a first degree of relative air humidity; and a second device (12) for processing the first air flow such that a second air flow to be completely or partially supplied to the person is produced. The temperature of the second air flow is lower and its degree of relative air humidity higher than that of the first air flow.

11 Claims, 2 Drawing Sheets

Figure 1:
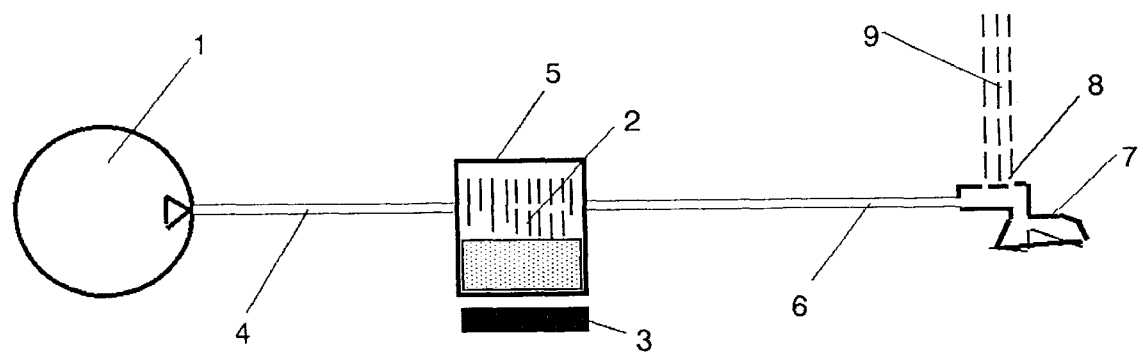

METHOD AND DEVICE FOR PRODUCING RESPIRATORY AIR WHICH IS HARMLESS TO HEALTH IN POSITIVE PRESSURE NASAL BREATHING APPARATUS

Nasal, positive-pressure respiratory devices are used for avoiding so-called obstructive sleep apnea.

Obstructive sleep apnea describes a collapse of the respiratory passages in the pharyngeal region that repeatedly occurs during sleep and that leads to respiratory arrests and, when it occurs frequently, instigates lasting damage to one's health due to lack of sleep and lack of oxygen.

In the positive-pressure respiratory devices known under the name nCPAP (nasal continuous positive airway pressure), a fan creates a constant pressure that is fed into the respiratory passages via a tube and a nasal mask. The positive pressure in the respiratory passages prevents the sealing of the pharyngeal musculature and thus eliminates the respiratory arrests.

For drawing off the expired, consumed air, a continuous stream of exhaust air is exhausted via fine exit openings along the breathing mask. The exhaust air exit openings must be made narrow so that a throttling effect is provided and the positive pressure does not collapse but rather only a predetermined amount of exhaust air exits.

In order to completely draw off the consumed air, the amount of exhaust air must be as large as the amount of expired air.

A health damaging effect results from positive-pressure respiration in that the air is warmed through the compression in the fan and that the relative humidity of the air is consequently reduced in accordance with the laws of nature. The dry air flowing continuously as a result of the stream of exhaust air dries out the mucous membranes of the respiratory passages and results thereby in continuous complaints (symptoms) comparable to a cold.

In order to avoid these problems, it is known to employ an air humidifier between the fan and the breathing mask.

In the early time of nasal, positive-pressure respiration, complex, regulated respiratory air humidifiers were used for this purpose, i.e. as are used in intensive care medical treatment.

In the meantime, a home, positive-pressure respiration during sleep has been shown to be a matter of life or death for tens of thousands of sleep apnea sufferers.

For this purpose, the complex, respiratory air humidifiers of intensive care medical treatment are too complicated and too expensive.

It thus became known to use so-called cold air humidifiers, wherein the air stream coming from the fan flows through a closed housing in which water is bubbled by means of a pump.

Since, however, it was shown during their use that the drying out of the mucous membranes in the respiratory passages could not be sufficiently avoided using the cold air humidifiers, so-called warm air humidifiers are primarily used at the present time, as is described in the instruction manual for PRIESS med. Technik's "Sullivan Atemgasanfeuchter (respiratory gas humidifier) Model HC 100," said firm residing at Karstrasse 17a, 41068 Mönchengladbach, Germany.

In FIG. 1 of the drawings, this prior art is illustrated schematically.

The fan 1 creates an air stream with a positive pressure of approx. 3 to 18 mbars, whereby the air stream heats up by approx. 1 to 2° C. over the ambient temperature. The air stream is fed via a tube 4 from the fan 1 to the air humidifier 5 and is further led from there, again via a tube 6, to the nose mask 7 and the fine exit openings 8 for the exhaust air stream 9, In the evaporation container 2 of the air humidifier, the water filled thereinto is evaporated by an electric heater 3. The air stream flowing therethrough accepts this water vapor in the evaporation container 2 and is thus simultaneously warmed by approx. 4 to 60° C. over the ambient temperature.

With such warm air humidifiers, a sufficient humidification of the respiratory air is achieved to avoid the drying out of the mucous membranes.

The warm humidification of the respiratory air, however, creates the following serious problems:

Through the warm humidification, the air that had already been warmed by the fan is warmed even more. The inhalation of this warm and humid air results in subjective respiratory distress and results thus in frequent sleep interruption and subsequently in significant problems in falling asleep.

Since the temperature of the warm, humidified air is higher than the ambient room temperature when it exits the humidifying container, condensation forms in the respiratory tube 6 and in the nose mask 7. In order to avoid the formation of (bacterial) cultures (colonies) that are dangerous to one's health as a result of this humidity, the tube 6 must be thoroughly washed and dried daily.

A serious problem results furthermore along the fine exit openings 8 for the exhaust air 9. Since the exhaust air 9 expands when it exits and, as a result, cools down adiabatically, further condensation from the humidity-saturated air forms in the fine exit air openings 8 and partially blocks these. As a result, the expired air is no longer sufficiently exhausted. The result is sleep and health disorders due to lack of oxygen.

Regarding the prior art, further reference is made to DE-C-6 34 919, which relates to a breathing chamber with cooled air, and to WO-A-9 320 874, which relates to an apparatus for destroying microorganisms.

The object of the invention is to provide an apparatus for creating respiratory air for home positive pressure—CPAP (Continuous positive pressure) respiration of persons with obstructive sleep apnea syndrome such that the occurrence of condensation is avoided during the creation of medically sound air humidity of the respiratory air.

For solving this problem, the features cited in claim 1 are provided. Preferred embodiments of the invention can be found in the dependent claims.

Before going into further advantages of the invention, it will be noted in regard to the aforementioned prior art that an air stream under positive pressure is created by the apparatus in accordance with the invention that is subjected to treatment prior to its introduction to the nose mask and the exit openings, said treatment being a humidifying treatment in the case of the prior art.

The sufficient air humidity is achieved by simple means without having to accept the deficiencies of the known positive-pressure respiration devices: the increased temperature of the respiratory air; the danger of the formation of health-threatening bacteria and lack of oxygen due to the blockage of the air exit openings through condensation.

The relative air humidity is known to be determined by the air temperature for invariant, absolute air humidity. This law of nature results in the damaging reduction of the relative air humidity through the warming by approx. 1 to 20° C. during the creation of the positive pressure in the fan of the positive-pressure respiratory device.

If the air supplied by the fan is now cooled with suitable means by approx. 5° C., the relative air humidity is then higher than prior to the compression. Since the temperature of the cooled air is then approx. 3° C. lower than the ambient temperature, condensation does not form in either the breathing tube or in the exhaust air slits of the nose mask due to the high relative air humidity.

The air tube must not longer be washed out and dried daily. The exhausting of the consumed respiratory air is not hindered by condensation in the exhaust air openings. The lack of oxygen as a result of insufficient drawing off of the exhaust air is thus avoided.

The cooled respiratory air gives the subjective impression of being fresh and allows a restful sleep.

Furthermore, the cooled air stream in accordance with the invention draws less humidity from the mucous membranes in accordance with the laws of nature than an air stream of the same relative air humidity but higher temperature of the known methods.

The cooling of the respiratory air is carried out in accordance with the invention via a heat exchanger, whereby the air stream supplied by the fan flows through a cooling profile or section (heat sink) in a closed housing.

The amount of heat that is to be drawn off from the air stream of max. 30 liters per minute is only 3.25 W when the temperature is reduced by 5° C. and can, in accordance with the invention, be drawn off using typical commercial Peltier elements.

The cold side of the Peltier element is thermally connected to the inner cooling profile (heat sink) of the heat exchanger. The heat from the hot side of the Peltier element can drawn off to the ambient air by means of an aired, outer cooling profile (heat sink).

Starting from the prior art of FIG. 1, an embodiment of the invention is described in more detail below based on FIGS. 2–4 of the drawings. These show:

FIG. 1: the prior art

Figure 2:
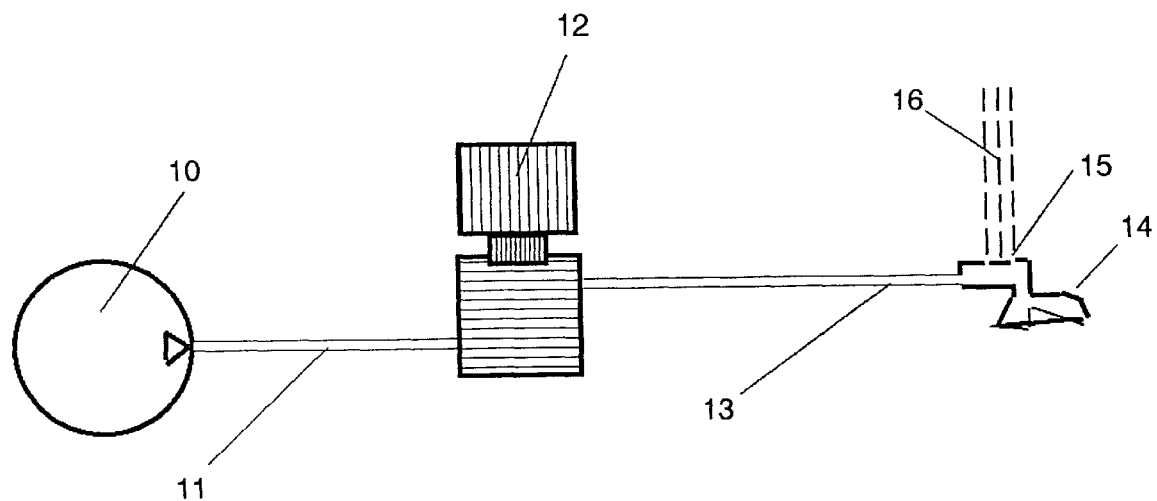
Figures 3, 4:
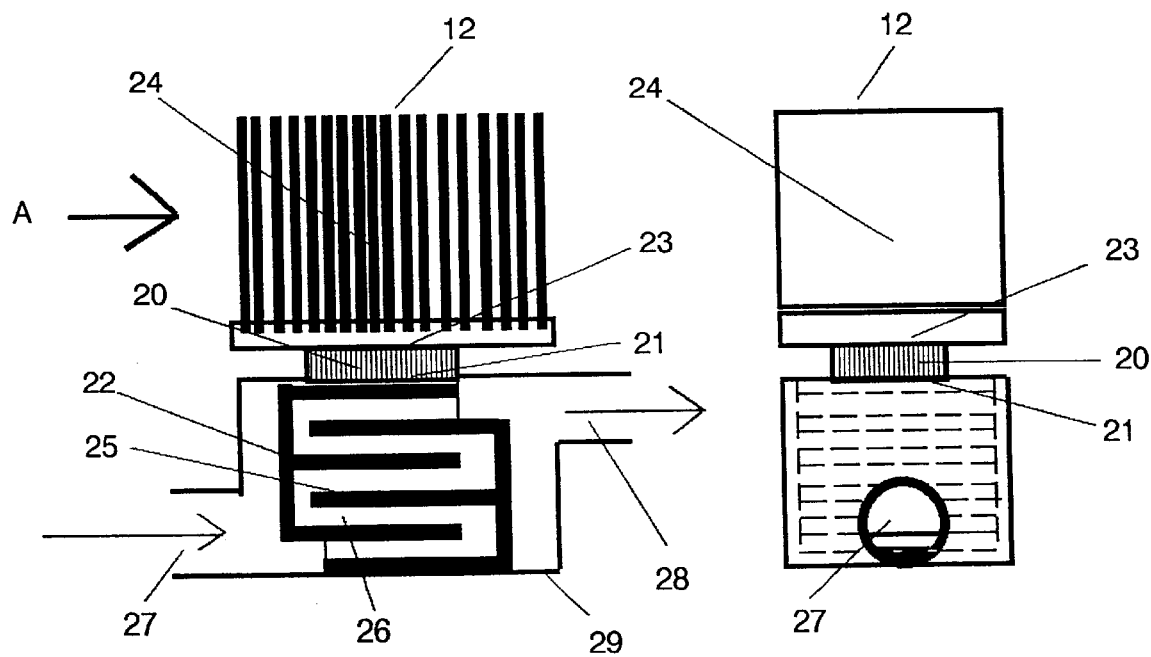

FIG. 2: the schematic construction of a nasal, positive-pressure respiratory apparatus FIG. 3: the schematic construction of the heat exchanger and FIG. 4: a view in the direction of A in FIG. 3.

In accordance with FIG. 2, an air stream in created by the fan 10 with a positive pressure between 3 and 18 mbars depending on the settings and led via the tube 11 to the heat exchanger 12. Through the compression, the air stream is heated between 1 to 2° C. relative to the ambient temperature depending on the positive pressure, and the relative humidity is thus reduced in accordance with the laws of nature relative to its condition when sucked in. The air stream is cooled in the heat exchanger 12 by approx. 3° C. below the ambient temperature. Thus, the relative air humidity of the air stream is increased by approx. 20% relative to its condition when sucked in. The air stream is led via the tube 13 to the nose mask 14 and the fine exit openings 15 for the exhaust air stream 16. Due to the higher ambient temperature, condensation from the air stream does not form in the tube 13 or in the fine exit openings 15. The fine exit openings 15 for the exhaust air stream 16 remain free such that the respiratory air is rich in oxygen and pleasing due to its being cooled.

The heat exchanger 12 in accordance with FIG. 3 and 4 consists essentially of a Peltier element 20 whose cold side 21 is thermally connected to the cooling profiles (heat sinks) 22 and 25 made of metal of higher thermal conductivity, for example aluminium, and whose hot side 23 is connected with a further cooling profile (heat sink) 24 made of metal of higher thermal conductivity.

Via the cooling profile 24, the air stream heat electrically pumped via the Peltier element 20 from the cold side 21 to the hot side 23 and the electrical power loss of the Peltier element 20 is drawn off to the ambient air.

The two E-formed cooling profiles 22 and 25 thermally connected with the cold side 21 of the Peltier element 20 form a meandering cooling channel 26 between the air entrance 27 and the air exit 28 for the air stream supplied by the fan 10.

The air entrance 27 and the air exit 28 of the housing 29 is formed pipe-shaped for connecting the tubes. The air entrance 27 is located at the position of the cooling channel farthest away from the Peltier element 20, and the exit 28 at the location closest to the Peltier element. Thus, a nearly constant temperature gradient to the cooling profiles 22 and 25 results for the continuous cooling of the air stream in the meandering cooling channel 26, and thus a particularly favorable cooling effect of the heat exchanger results.

Naturally, other embodiments (shapes) for the cooling profiles are possible. In particular, the profiles could be enlarged through further ribs for enlarging the cooling area.

In summary, one can say that the invention relates to a nasal, positive-pressure respiration device in which a treated air stream comprising a positive pressure is fed to the person to be treated, whereby a first apparatus 10 serves to create a first air stream that comprises a predetermined first temperature and a first relative air humidity, and whereby a second apparatus 12 processes the first air stream such that a second air stream is created that is entirely or partially fed to the person, the temperature of which air stream is lower and whose relative air humidity is higher than that of the first air stream.

Preferably, the first apparatus is a fan 10 that warms the sucked-in ambient air such that the first air stream possesses the predetermined first temperature. The second apparatus is preferably a heat exchanger that preferably works according to the Peltier principle.

In accordance with a further embodiment, the second apparatus is a single Peltier element that is preferably formed on the basis of a semiconductor and that possesses a flat form of approx. 4×4 cm length as well as a thickness of 5 to 6 mm. The nasal, positive-pressure respiratory device also preferably provides for the ambient air warmed via the air stream creating apparatus, i.e. the fan 10, by approx. 1 to 2° C. to be cooled by approx. 3 to 6° C., preferably 5° C., via the Peltier element such that the second air stream exiting from the Peltier element is 2 to 4° C., preferably approx. 3° C., colder than the air sucked in from the surroundings, wherein the relative air humidity of the second air stream exiting from the Peltier element lies approx. 30 to 40% higher than the relative air humidity of the air sucked in, wherein the second air stream exiting from the Peltier element is warmed along the path to the breathing mask, if at all, and thus possesses a somewhat reduced relative humidity, whereby however no condensation is formed, such that the exit openings 8 or slits for the exhaust air present behind a breathing mask supplied totally or partially by the second air stream are also not blocked since no condensation is formed.

Preferably, the Peltier element 20 is connected on its hot side 23 with the cooling profile 24, and the cold side 21 comprises cooling profiles such that the cooling channel 26 for the flowing through of air is formed. The cooling channel 26 is, as stated, preferably has a meandering shape and is formed through two intermeshed cooling profiles 22, 25.

The nasal, positive-pressure respiratory device using a heat exchanger, in particular a Peltier element, comprises, in accordance with the invention, an apparatus 10 that creates the positive pressure of the respiratory air, said apparatus 10 being in connection via tube connections 11, 13 with a mask 14 that comprises fine exit openings 15 for the exhaust air stream, wherein a heat exchanger is introduced in the connection between the apparatus 10 creating the positive pressure and the mask 14.

It is also possible to provide a nasal, positive-pressure respiratory device using a heat exchanger, in particular a Peltier element, such that an apparatus 10 creating the positive pressure of the respiratory air is provided that is connected via tube connections 11, 13 with a mask 14 that comprises fine exit openings 15 for the exhaust air stream, and wherein the Peltier element is located in front of the apparatus 10 for creating a positive pressure. Furthermore, the nasal, positive-pressure respiratory device using a heat exchanger, in particular a Peltier element, can be formed such that a Peltier is connected in circuit prior to and a further Peltier element is connected in circuit subsequent to the apparatus 10 creating the positive pressure of the respiratory air that is connected via tube connection 11, 13 with the mask 14 that comprises fine exit openings 15 for the exhaust air stream.

I claim:

1. A CPAP (Continuous Positive Air Pressure) respiratory apparatus for home positive pressure respiration of persons with obstructive sleep apnea syndrome comprising a fan for creating the positive pressure and a heat exchanger including a Peltier element having a hot side and a cold side, the heat exchanger being inserted into the air stream of the fan, said heat exchanger cooling the air stream supplied by the fan to a temperature 2–4 degrees Celcius below ambient temperature before it is supplied to a nose mask and exit openings; the heat exchanger further comprising first and second cooling profiles with the Peltier element being connected to the first cooling profile and the hot side being connected to the second cooling profile.

2. The CPAP (Continuous Positive Air Pressure) respiratory apparatus of claim 1 characterized in that the first cooling profiles have an "E" shape and form a meandering cooling channel for the air stream supplied by the fan between an air entrance and an air exit.

3. The CPAP (Continuous Positive Air Pressure) respiratory apparatus of claim 1 characterized in that the supplied air stream is cooled by 2 to 4° C. below the ambient temperature.

4. The CPAP (Continuous Positive Air Pressure) respiratory apparatus of claim 3 characterized in that the supplied air stream is cooled by 3° C. below the ambient temperature.

5. The CPAP (Continuous Positive Air Pressure) respiratory apparatus of claim 1 characterized in that the supplied air stream is cooled by 3 degrees Celcius below ambient temperature.

6. In a method for CPAP (Continuous Positive Air Pressure) for home positive pressure respiration of persons with obstructive sleep apnea syndrome, the improvement comprising: providing a fan and generating a positive pressure air stream from the fan and providing a nose mask having exit openings and operatively connecting the nose mask to the positive pressure air stream; providing a heat exchanger and inserting the heat exchanger into the positive pressure air stream; conveying the air stream from the heat exchanger through a breathing tube to the nose mask and exit openings therein, cooling the positive pressure air stream with the heat exchanger to a temperature minus 2–4 degrees Celcius below ambient temperature thereby increasing the relative humidity of the air stream; supplying the cooled positive pressure air stream to the nose mask and exit openings for maintaining the respiratory air rich in oxygen; maintaining the exit openings open by avoiding any formation of condensation from the cooled positive pressure air stream in the breathing tube and in the exit openings; and facilitating an exhaust of exhaled air through the exit openings.

7. The method of claim 6 including providing cooling in the heat exchanger by a Peltier element.

8. The method of claim 7 including providing the heat exchanger with first and second cooling profiles.

9. The method of claim 8 including connecting the first cooling profile of the heat exchanger to a cold side of the Peltier element and connecting the second profile of the heat exchanger with a hot side of the Peltier element.

10. The method of claim 9 wherein the first cooling profile has an E-shape and forms a meandering cooling channel for the air stream supplied by the fan between an air entrance and an air exit.

11. The method of claim 6 including cooling the air stream to a temperature of 3° C. below the ambient temperature.

* * * * *